US 8,075,907 B2

(12) United States Patent
Kühn et al.

(10) Patent No.: US 8,075,907 B2
(45) Date of Patent: Dec. 13, 2011

(54) POLYMETHYLMETHACRYLATE REVISION BONE CEMENT

(75) Inventors: Klaus-Dieter Kühn, Marburg-Elnhausen (DE); Sebastian Vogt, Erfurt (DE); Hubert Büchner, Reinheim (DE)

(73) Assignee: Heraeus Kulzer GmbH, Hanau (DE)

( * ) Notice: Subject to any disclaimer, the term of this patent is extended or adjusted under 35 U.S.C. 154(b) by 483 days.

(21) Appl. No.: 12/017,499

(22) Filed: Jan. 22, 2008

(65) Prior Publication Data

US 2008/0213336 A1 Sep. 4, 2008

(30) Foreign Application Priority Data

Jan. 26, 2007 (DE) .......................... 10 2007 004 968

(51) Int. Cl.
*A61F 2/28* (2006.01)

(52) U.S. Cl. ........ 424/423; 424/422; 424/424; 424/484; 424/486

(58) Field of Classification Search ........................ None
See application file for complete search history.

(56) References Cited

U.S. PATENT DOCUMENTS

| 5,968,253 | A | * | 10/1999 | Poser et al. .................. 106/691 |
| 6,160,033 | A | | 12/2000 | Nies | |
| 2006/0292199 | A1 | * | 12/2006 | Kuhn et al. .................. 424/422 |

FOREIGN PATENT DOCUMENTS

| DE | 199 53 975 A1 | 5/2001 |
| DE | 600 05 049 T2 | 7/2004 |
| DE | 10 2004 049 121 A1 | 4/2006 |
| EP | 0 676 408 A1 | 10/1995 |
| JP | 3 502539 T | 6/1991 |
| JP | 5 253286 | 10/1993 |
| JP | 2001 503290 A | 3/2001 |
| JP | 2001 510369 A | 7/2001 |
| JP | 2006 102512 A | 4/2006 |

* cited by examiner

*Primary Examiner* — Brandon Fetterolf
*Assistant Examiner* — Dennis Heyer
(74) *Attorney, Agent, or Firm* — Norris, McLaughlin & Marcus, P.A.

(57) ABSTRACT

The invention relates to a PMMA revision bone cement having powder and liquid component, in which the powder component contains two or more granular antibiotics whose grain size distribution is equal in that the main screening fraction each of the individual antibiotics is in the same grain size range, in particular in the range of 100-250 μm or 150-250 μm.

9 Claims, No Drawings

POLYMETHYLMETHACRYLATE REVISION BONE CEMENT

The subject matter of the invention is a polymethylmethacrylate revision bone cement (PMMA revision bone cement).

Articular endoprostheses currently have a serviceable life of several years, e.g. 10-15 years on average in the case of cemented hip-joint prostheses. However, there are cases, in which the articular endoprostheses become loose undesirably prior to reaching the usual serviceable life. In this regard, a distinction is being made between septic and aseptic loosening. Microbial pathogens are not detectable in cases of aseptic loosening. Aseptic loosening may be due to a large variety of causes. Cases of aseptic loosening frequently are caused by abrasion on the sliding surfaces of the articular endoprostheses. The loosening process in septic loosening is elicited by microbial pathogens. In this regard, a distinction is made between early and late infections depending on the time of manifestation. Septic loosening is a very serious disease for the patient and, in addition, associated with very high costs. It is common to perform a revision in cases of aseptic and septic loosening. In this regard, a distinction is made between the one-stage and the two-stage revision. In cases of septic loosening, either cement-free revision prostheses or cemented revision prostheses and PMMA bone cements can find application in the one-stage and in the two-stage revision. In this regard, after detection of the pathogens that are present and preparation of an antibiogram, these PMMA bone cements should be supplied with suitable antibiotics. It is common in this regard to use combinations of two to three different antibiotics whose mechanisms of action against the detected microorganisms should differ as strongly as possible. These antibiotics are admixed to conventional PMMA bone cements by surgeons in a clinical setting or by pharmacists using largely aseptic conditions (H. Breithaupt: Lokale Antibiotikatherapie. In: Septische Knochenchirurgie. Eds. R. Schnettler, H.-U. Steinau, Georg Thieme Verlag Stuttgart New York, 2004). In this regard, it is desirable to achieve as-high-as-possible initial release of the antibiotics from the PMMA bone cement at the interface of bone cement/bone after the implantation.

Antibiotics-modified PMMA bone cements (polymethylmethacrylate bone cements) have been known since the 1960s based on the work of H. W. Buchholz and Kulzer (W. Ege, K.-D. Kuhn: Industrial development of bone cement—25 years of experience. In: Bone Cement and Cementing Technique. Eds. G. H. I. M. Walenkamp, D. W. Murray, Springer Verlag Heidelberg, 2001, in press; H. W. Buchholz, E. Engelbrecht: Ober die Depotwirkung einiger Antibiotika beim Vermischen mit dem Kunstharz Palacos. Chirurg 41 (1970) 511-515). These PMMA cements are widely accepted and in widespread use for the fixation of endoprostheses (K.-D. KOhn: Knochenzemente fur die Endoprothetik: ein aktueller Vergleich der physikalischen and chemischen Eigenschaften handelsOblicher PMMA-Zemente. Springer-Verlag Berlin Heidelberg New York, 2001). Following the implantation, the antibiotic that is integrated into the conventional PMMA bone cements is locally released more or less rapidly at the interface of bone cement/bone where it is to prevent bacterial colonization. It is desired to achieve as-high-as-possible initial release such that the minimal inhibitory concentration (MIC) of the antibiotic used therein with regard to the clinically relevant pathogens is safely reached and exceeded at the interface of bone cement/bone. By this means, the interface between the bone and the PMMA bone cement can be protected from microbial colonization for a period of multiple days after the implantation.

DE102004049121 (A1) proposes a PMMA bone cement that is characterized in that the powder component contains 0.1-5.0 mass percent of water-soluble, glass-like antibiotic/antibiotics granulates having a particle diameter in the range of 63-900 µm that are made up of mutually connected glass-like antibiotic/antibiotics primary particles having a particle diameter in the range of 1-70 µm.

It is the object of the invention to develop a PMMA revision bone cement that is supplied with two or more antibiotics and guarantees high initial release of all antibiotics contained in the cement after implantation.

The invention is based on the surprising finding that PMMA bone cements that contain two or more granular antibiotics show high initial antibiotics release provided the grain size distribution of the antibiotics used therein is approximately equal. Hereinafter, the term, granular antibiotics, shall be taken to mean antibiotics grains that are in the solid state of aggregation at room temperature and are regularly or irregularly shaped. The antibiotics grains can be either crystalline or amorphous. It is also feasible for the antibiotics grains to be partially crystalline.

The object was met by developing a PMMA revision bone cement. The powder component of this PMMA revision bone cement having powder and liquid component contains two or more granular antibiotics whose grain size distribution is equal in that the main screening fraction each of the individual antibiotics is in the same grain size range.

The main screening fraction of the antibiotics preferably each comprises at least 50 weight percent of the respective antibiotic.

The grain size range of the main screening fraction of the individual antibiotics is, in particular, 100 to 250 pm or 150 to 250 µm.

The grain size distribution is equal if the screening fractions of the individual antibiotics are approximately equal. However, it shall be sufficient if the main screening fractions of the antibiotics have the same grain size. Main screening fractions are, in particular, those of each at least 50 weight percent of each antibiotic.

The term, powder component of the PMMA bone cement, shall be understood to mean a mixture of at least one powder-like polymethylmethacrylate or a copolymer made up of methyl-methacrylate and methylacrylate, a powder-like X-ray opaquer, such as zirconium dioxide and/or barium sulfate, and a radical initiator, such as dibenzoylperoxide. If applicable, ingredients of the powder component can be dyed by a pharmaceutically acceptable dye. After mixing with the liquid component that is made up of methylmethacrylate (MMA) in which a radical activator, such as N,N-dimethyl-p-toluidine is dissolved, the powder component yields a paste that can be deformed in a plastic fashion and self-hardens within but a few minutes due to the commencing radical polymerisation of the methylmethacrylate.

The PMMA bone cement manufactured according to the invention showed very high antibiotic release under in vitro conditions at 37° C.

The granular antibiotics consist, e.g. of at least one representative from the groups of aminoglycoside antibiotics, lincosamide antibiotics, fluoroquinolone antibiotics, glycopeptide antibiotics, and nitroimidazoles. The antimicrobially effective chemotherapeutics from the group of nitroimidazoles are also understood to be antibiotics, in a simplifying manner. These chemotherapeutics act mainly bactericidal against anaerobic pathogens and protozoa.

Within the scope of the invention, it is preferred for the granular antibiotics to consist of gentamicin sulfate, gentamicin hydrochloride, amikacin sulfate, amikacin hydrochloride, tobramycin sulfate, tobramycin hydrochloride, clindamycin hydrochloride, lincosamine hydrochloride, moxifloxacin, ciprofloxacin, teicoplanin, vancomycin, ramoplanin, dalbavancin, daptomycin, tigecyglin, metronidazole, tinidazole, and omidazole. Aside from these water-soluble antibiotics salts and antibiotics, sparingly water-soluble salt forms of the antibiotics, such as, for example, flavone phosphates, palmitates, myristates and laurates, can be used just as well or additionally be contained therein. Moreover, it is also feasible to use or add antibiotics from the group of the oxazolidones, such as linezolid.

Moreover, it is advantageous if the granular antibiotics can, in addition, contain polyvinylpyrrolidone and/or polyethylene glycol and/or polyethyleneoxide and/or maltose and/or sorbitol and/or mannitol as excipients, if applicable. It is also within the scope of the invention if the granular antibiotics are stabilized by other toxicologically acceptable polymers, such as gelatin, collagen, and dextran. The extended scope of the invention can also include granular antibiotics that have been glued or cemented by adhesive excipients into antibiotics granulates having particle sizes in the range of 63-900 μm, as described in DE102004049121 A1.

The invention shall be illustrated on the basis of the following example though without limiting the scope of the invention. Like in all of the description, the parts and specified percentages refer to the weight, unless stated otherwise.

EXAMPLE 1

Release tests were conducted using sample bodies in order to test the PMMA bone cement according to the invention. The sample bodies were prepared such that, initially, 40.0 g of the powder component of the bone cement, Palacos R, each were mixed with Variant a) 0.80 g gentamicin sulfate (corresponds to 0.50 g gentamicin base; screening fractions: 2%<63 μm; 3% 63-100 μm; 93% 100-250 μm; 2%>250 μm)+2.17 g vancomycin hydrochloride (corresponds to 2.00 g vancomycin base; screening fractions: 43%<63 μm; 62% 63-100 μm; 5% 100-250 μm; 0%>μm)

Variant b) 0.80 g gentamicin sulfate (corresponds to 0.50 g gentamicin base; screening fractions: 2%<63 μm; 3% 63-100 μm; 93% 100-250 μm; 2%>250 μm)+2.17 g vancomycin hydrochloride (corresponds to 2.00 g vancomycin base; screening fractions: 3%<63 μm; 25% 63-100 μm; 55% 100-250 μm; 19%>250 μm).

Subsequently, these modified powder components each were mixed with 20.0 g of the monomer component. Thus was formed a green paste that was pasted into hollow molds and hardened therein within few minutes. The cylinder-shaped sample bodies thus generated had a height of 1 cm and a diameter of 2.5 cm. Five sample bodies were manufactured per each cement variant. The sample bodies were stored separately in 20 ml distilled water each at 37° C. Every day all of the release medium was removed and the quantity of gentamicin released into the medium was determined. Subsequently, the sample bodies were stored again in 20 ml fresh distilled water at 37° C. each. A TDX Analyzer made by Abott was used to determine the released gentamicin and the released vancomycin. The mass of gentamicin base and vancomycin base released per gram of sample body in each case was specified in the following table as a function of the storage time of the sample bodies in the release medium.

| Storage time [d] | | Released antibiotics | | |
|---|---|---|---|---|
| | | 1 d | 3 d | 5 d |
| Variant 1 | Gentamicin | 197 μg/g | 14 μg/g | 7 μg/g |
| | Vancomycin | 366 μg/g | 12 μg/g | 6 μg/g |
| Variant 2 | Gentamicin | 276 μg/g | 11 μg/g | 14 μg/g |
| | Vancomycin | 630 μg/g | 26 μg/g | 19 μg/g |

What is claimed is:

1. A polymethylmethacrylate (PMMA) revision bone cement having powder and liquid components, wherein the powder component comprises two or more granular individual antibiotics whose grain size distribution is equal in that a main screening fraction of each of the individual antibiotics is in the same grain size range, wherein the main screening fraction of the antibiotics each comprises at least 50 weight percent of each antibiotic, and wherein the grain size range of the main screening fraction of the individual antibiotics is 100 to 250 gm.

2. PMMA revision bone cement according to claim 1, wherein the grain size range of the main screening fraction of the individual antibiotics is 150 to 250 μm.

3. PMMA revision bone cement according to claim 1, wherein the granular antibiotics are one or more members selected from the group consisting of gentamicin sulfate, gentamicin hydrochloride, amikacin sulfate, amikacin hydrochloride, tobramycin sulfate, tobramycin hydrochloride, clindamycin hydrochloride, lincosamine hydrochloride, moxifloxacin, ciprofloxacin, teicoplanin, vancomycin, ramoplanin, dalbavancin, daptomycin, tigecyglin, metronidazole, tinidazole, and omidazole.

4. PMMA revision bone cement according to claim 1, wherein the granular antibiotics are selected from the group consisting of sparingly water-soluble salt forms of antibiotics from the group of antibiotics flavone phosphates, antibiotics palmitates, antibiotics myristates, and antibiotics laurates.

5. PMMA revision bone cement according to claim 1, wherein the granular antibiotics are selected from the group consisting of oxazolidones.

6. PMMA revision bone cement according to claim 1, wherein the granular antibiotics component further comprises at least one excipient selected from the group consisting of polyvinylpyrrolidone, polyethyleneglycol, polyethyleneoxide, maltose, sorbitol, and mannitol.

7. PMMA revision bone cement according to claim 1, wherein the granular antibiotics component further comprises at least one excipient selected from the group consisting of the toxicologically acceptable polymers, gelatin, collagen, and dextran.

8. PMMA revision bone cement according to claim 1, wherein at least a part of the granular antibiotics is glued or cemented by adhesive excipients into antibiotics granulates having particle sizes in the range of 63-900 μm.

9. A polymethylmethacrylate (PMMA) revision bone cement having powder and liquid components, wherein the powder component comprises granules of a first antibiotic and granules of a second antibiotic, wherein the granules of said first antibiotic are present in said powder component in a plurality of grain size fractions, and the granules of said second antibiotic are also present in said powder component in a plurality of grain size fractions; wherein one of said grain size fractions of said first antibiotic is designated as a main screening fraction of said first antibiotic, and one of said grain size fractions of said second antibiotic is designated as a main screening fraction of said second antibiotic; wherein the main screening fraction of said first antibiotic is present in an amount of at least 50 percent by weight based on a total weight of the first antibiotic in the powder component, and the main screening fraction of said second antibiotic is also present in an amount of at least 50 percent by weight based on a total weight of the second antibiotic in the powder component; and wherein the grain size of the main screening fraction of said first antibiotic is 100 to 250 µm, and the grain size of the main screening fraction of said second antibiotic is also 100 to 250 µm.

* * * * *